(12) United States Patent
Kubler et al.

(10) Patent No.: US 9,764,870 B2
(45) Date of Patent: Sep. 19, 2017

(54) DEVICE FOR THE AUTOMATED OPENING OF FLIP TUBES

(75) Inventors: Walter Kubler, Schweiz (CH); Rainer Beckbissinger, Schweiz (CH); Urs Muller, Schweiz (CH)

(73) Assignee: Hamilton Bonaduz AG, Schweiz (CH)

(*) Notice: Subject to any disclaimer, the term of this patent is extended or adjusted under 35 U.S.C. 154(b) by 785 days.

(21) Appl. No.: 13/698,554

(22) PCT Filed: May 18, 2011

(86) PCT No.: PCT/EP2011/058041
§ 371 (c)(1),
(2), (4) Date: Feb. 1, 2013

(87) PCT Pub. No.: WO2011/144658
PCT Pub. Date: Nov. 24, 2011

(65) Prior Publication Data
US 2013/0118118 A1    May 16, 2013

(30) Foreign Application Priority Data
May 19, 2010    (DE) .................. 10 2010 029 136

(51) Int. Cl.
*B01L 3/00*    (2006.01)
*B65B 69/00*    (2006.01)
*G01N 35/04*    (2006.01)

(52) U.S. Cl.
CPC .......... *B65B 69/00* (2013.01); *B01L 3/50825* (2013.01); *G01N 35/04* (2013.01);
(Continued)

(58) Field of Classification Search
CPC ............ B01L 3/523; B65B 7/26; B65B 43/38
(Continued)

(56) References Cited

U.S. PATENT DOCUMENTS 356,115 A * 1/1887 Frothingham .......... E05F 5/025
16/85
3,098,721 A  7/1963 Jewell
(Continued)

FOREIGN PATENT DOCUMENTS

DE    3204584    9/1982
DE    3346517    8/1984
(Continued)

OTHER PUBLICATIONS

German Search Report of 10 2010 029 136.6 Nov. 11, 2010.
(Continued)

*Primary Examiner* — Thanh Truong
*Assistant Examiner* — Patrick Fry
(74) *Attorney, Agent, or Firm* — Rankin, Hill & Clark LLP

(57) ABSTRACT

A tool device for the automated opening of flip tubes including an actuating plunger which is provided and configured to move the actuating portion at least in open direction and thereby to exert an opening moment on the lid portion, and wherein the device further includes a damping means which is configured to exert a damping moment on the container lid at least during a period of the actuation of the actuating portion by the actuating plunger, which damping moment is less in amount and is in an opposite direction compared to the opening moment.

26 Claims, 9 Drawing Sheets

Figure 1:
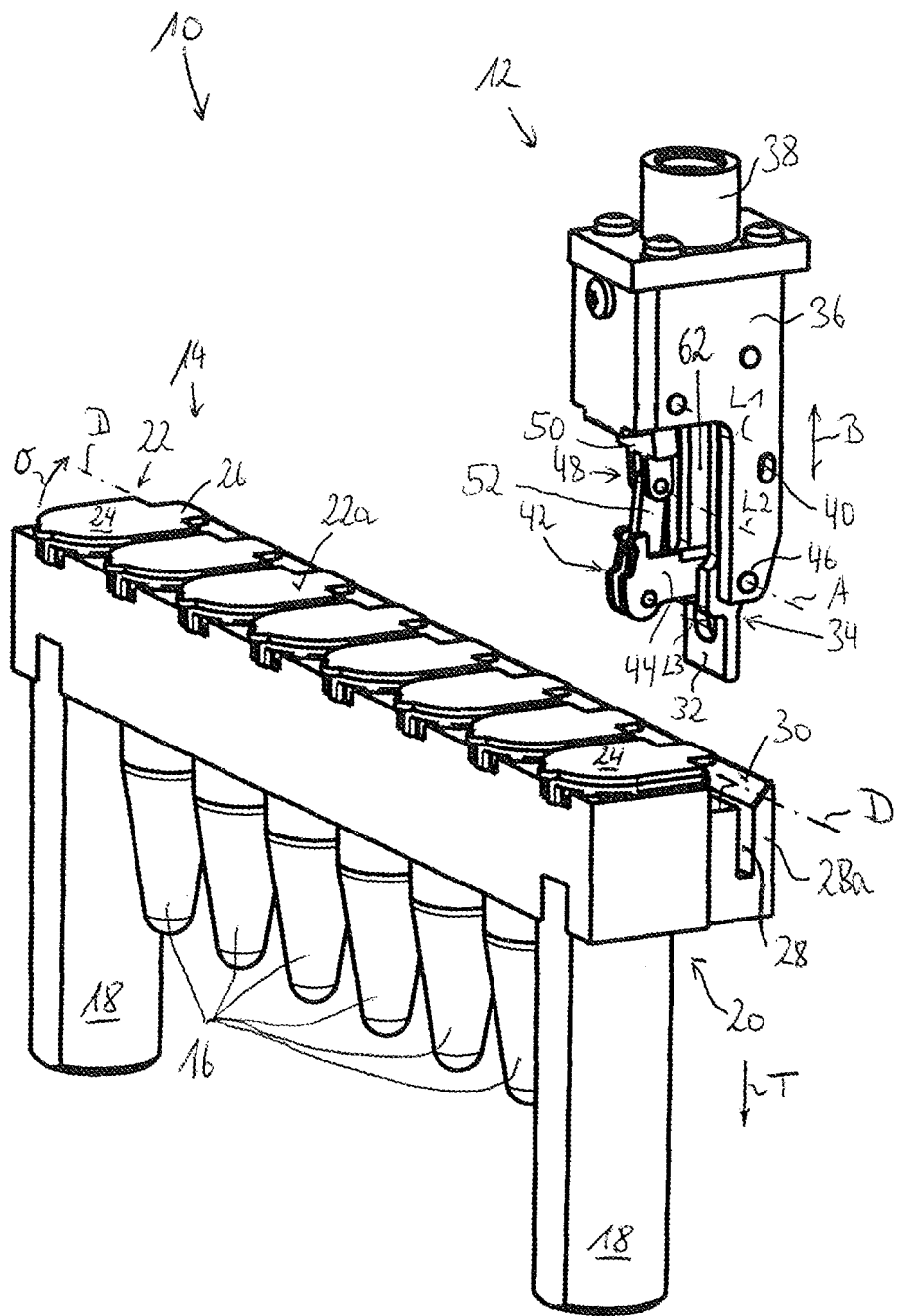

(52) U.S. Cl.
CPC .............................. *B01L 2300/043* (2013.01);
*G01N 2035/0405* (2013.01)

(58) Field of Classification Search
USPC ............... 53/381.1, 381.4, 382.1, 382.2, 468
See application file for complete search history.

(56) References Cited

U.S. PATENT DOCUMENTS

| | | | |
|---|---|---|---|
| 3,993,452 A | 11/1976 | Moulding | |
| 4,455,280 A * | 6/1984 | Shinohara | G01N 35/1002 141/154 |
| 4,515,286 A | 5/1985 | Ushikubo | |
| 5,248,056 A | 9/1993 | Shaw | |
| 5,271,897 A * | 12/1993 | Wurschum | B01L 3/50853 422/561 |
| 5,289,930 A | 3/1994 | Inouye | |
| 5,358,691 A | 10/1994 | Clark et al. | |
| 5,628,962 A * | 5/1997 | Kanbara | B01L 99/00 215/235 |
| 6,827,904 B2 * | 12/2004 | Kitagawa | B65D 21/0204 215/211 |
| 6,866,820 B1 | 3/2005 | Otto et al. | |
| 8,501,094 B2 * | 8/2013 | Mototsu | B01L 3/50825 422/547 |
| 2004/0170532 A1 | 9/2004 | Takahashi et al. | |
| 2006/0216210 A1 | 9/2006 | Dumitrescu et al. | |
| 2007/0110624 A1 * | 5/2007 | Lare | G01N 35/00 422/400 |
| 2008/0286160 A1 | 11/2008 | Ohashi et al. | |
| 2010/0080732 A1 * | 4/2010 | Mototsu | B01L 3/50825 422/63 |

FOREIGN PATENT DOCUMENTS

| | | |
|---|---|---|
| DE | 102009020811 | 11/2010 |
| EP | 0523425 | 1/1993 |
| EP | 0543638 | 5/1993 |
| EP | 0566196 | 10/1993 |
| EP | 0703457 | 3/1996 |
| EP | 1046915 | 10/2000 |
| EP | 1923705 | 5/2008 |
| EP | 2168683 | 3/2010 |
| JP | S57-177998 | 5/1956 |
| JP | H05-065898 | 8/1993 |
| JP | 2001343392 | 12/2001 |
| JP | 2006272248 | 10/2006 |
| JP | 2007511420 | 5/2007 |
| JP | 2010509589 | 3/2010 |
| WO | 9609554 | 3/1996 |
| WO | 2005029094 | 3/2005 |

OTHER PUBLICATIONS

International Search Report of PCT/EP2011/058041 dated Jul. 20, 2011.
JP Office action filed in application No. 2013-510615 mailed Mar. 31, 2015.

* cited by examiner

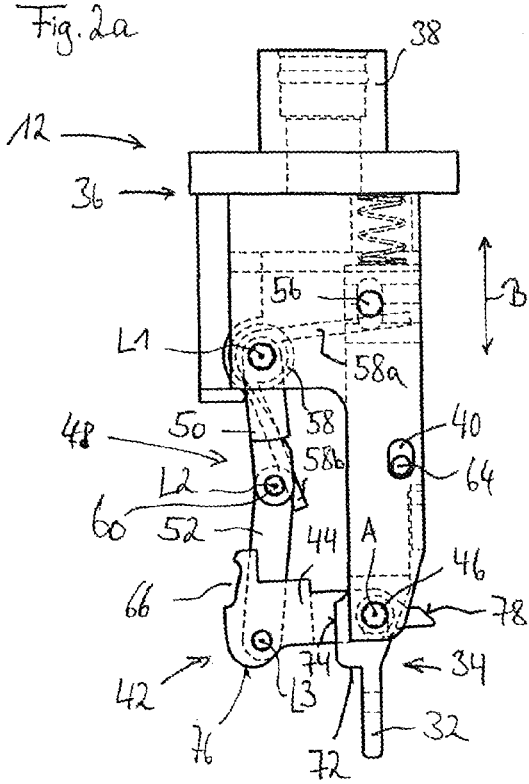
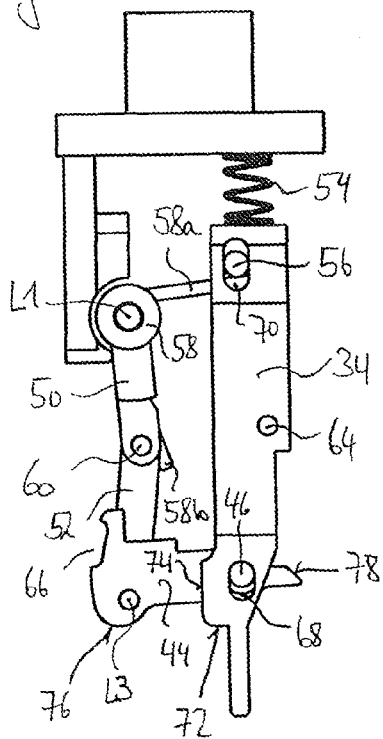
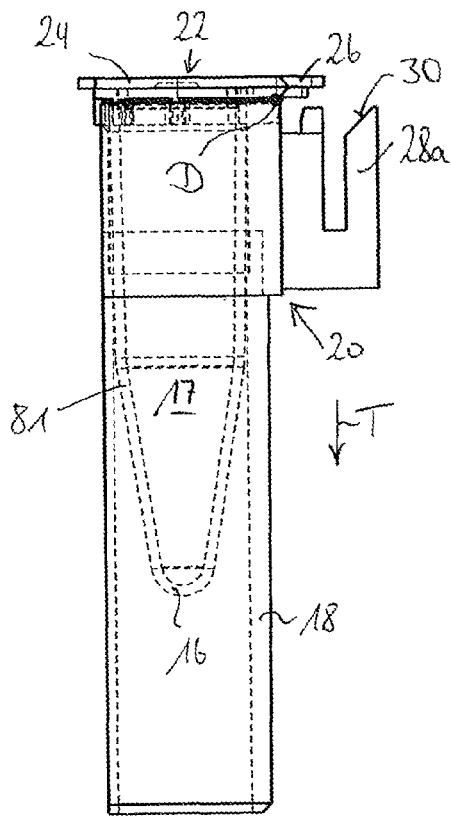

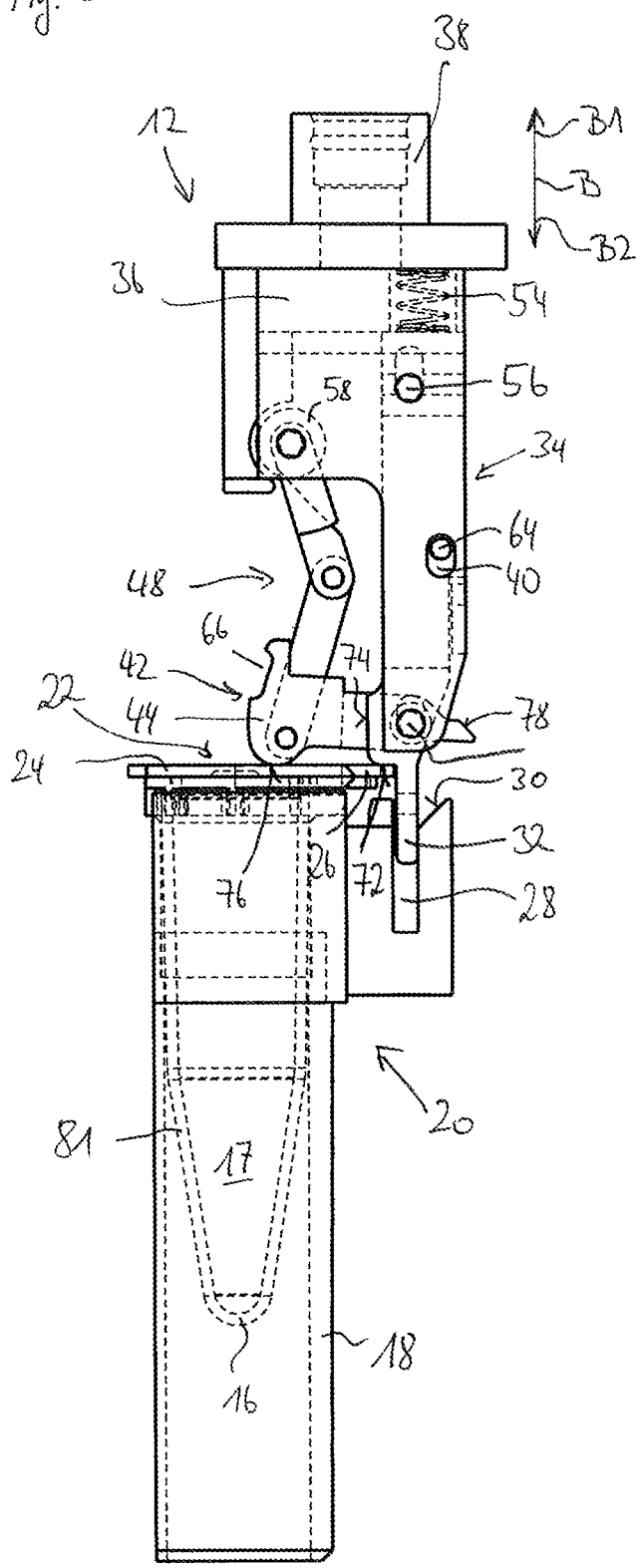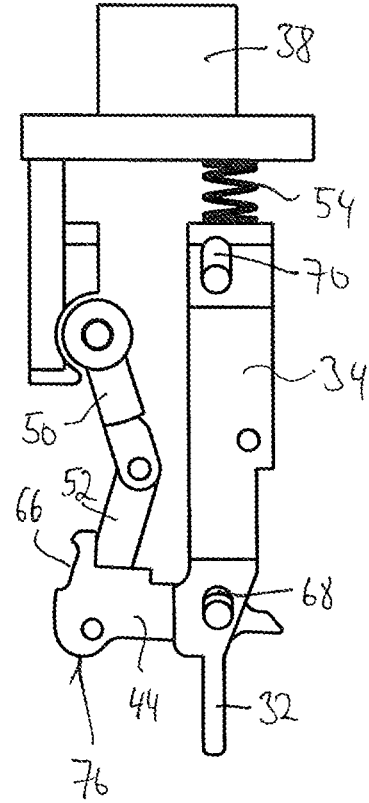

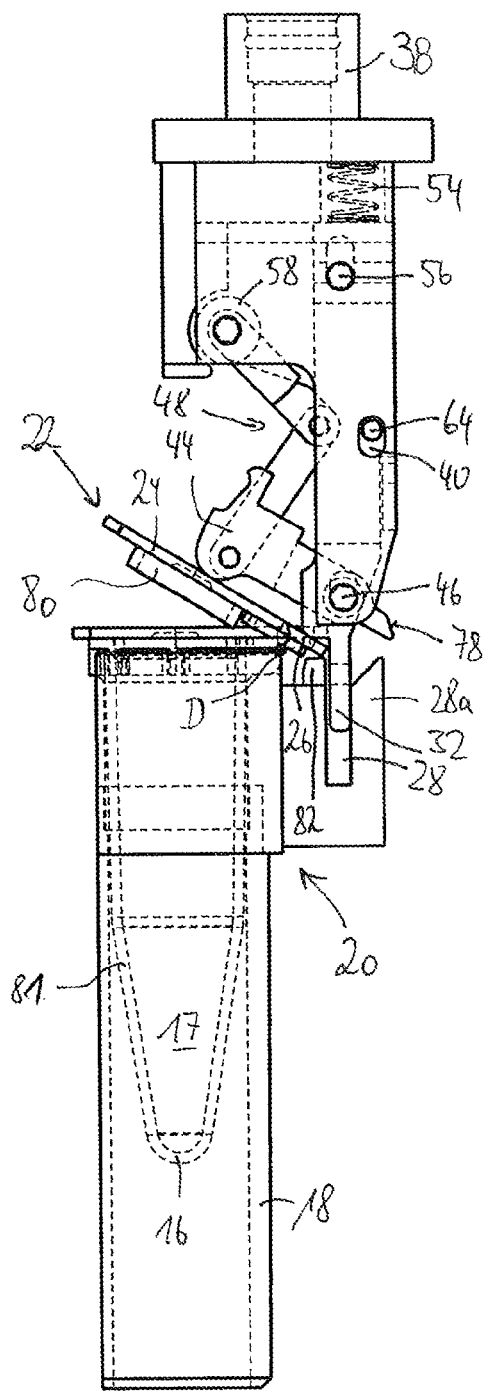
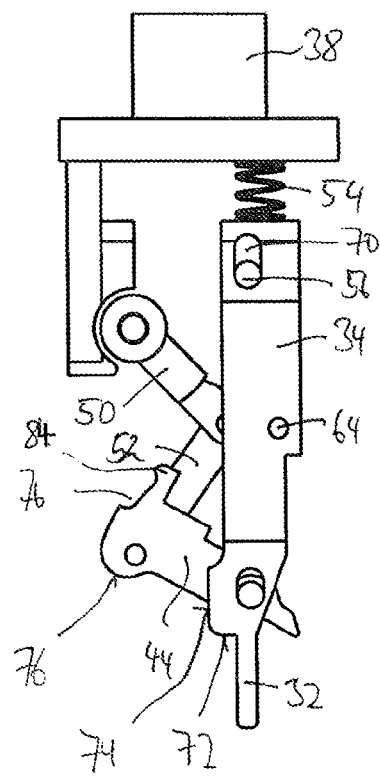
Fig. 4a:
Fig. 4b:

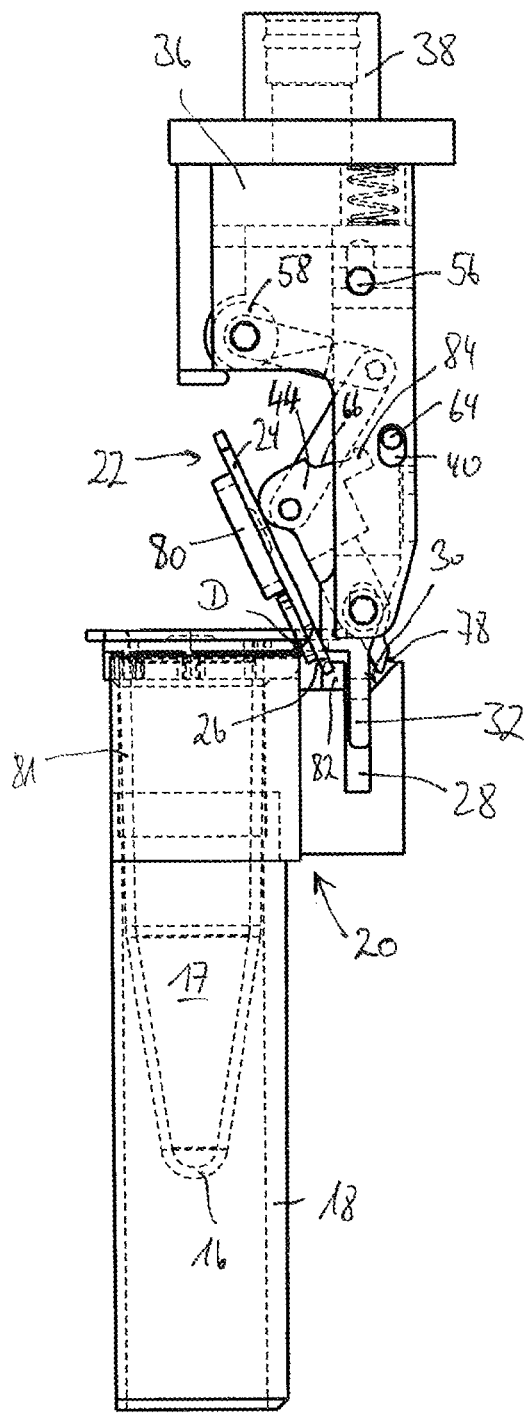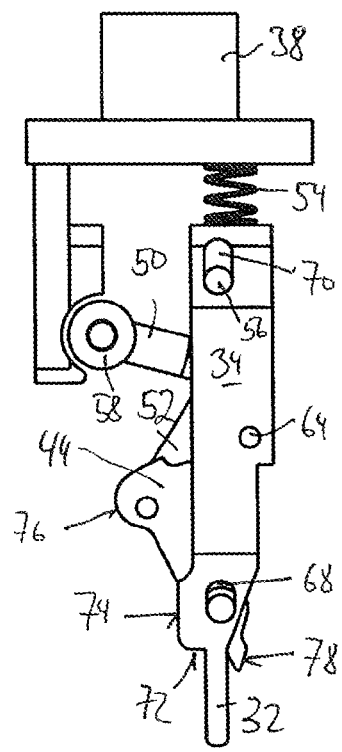

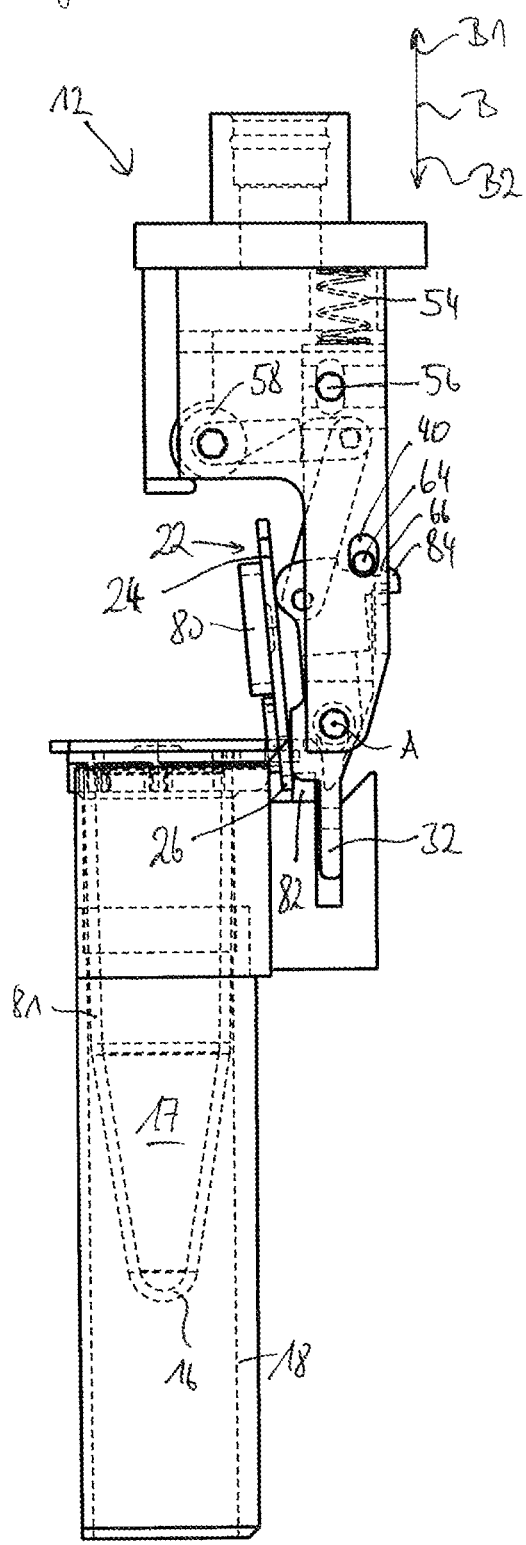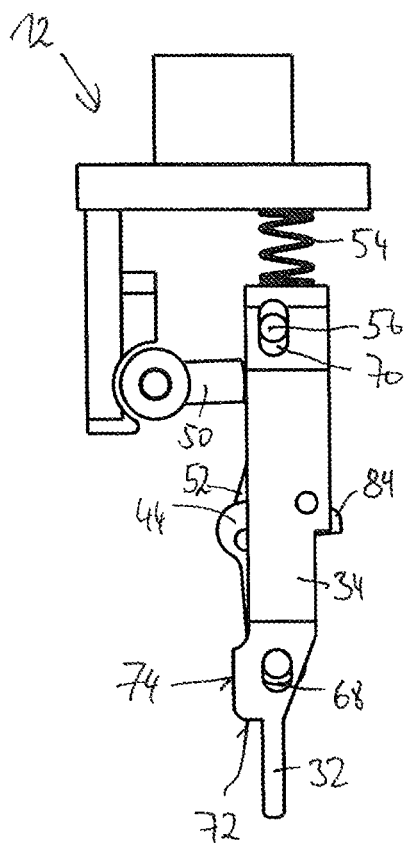

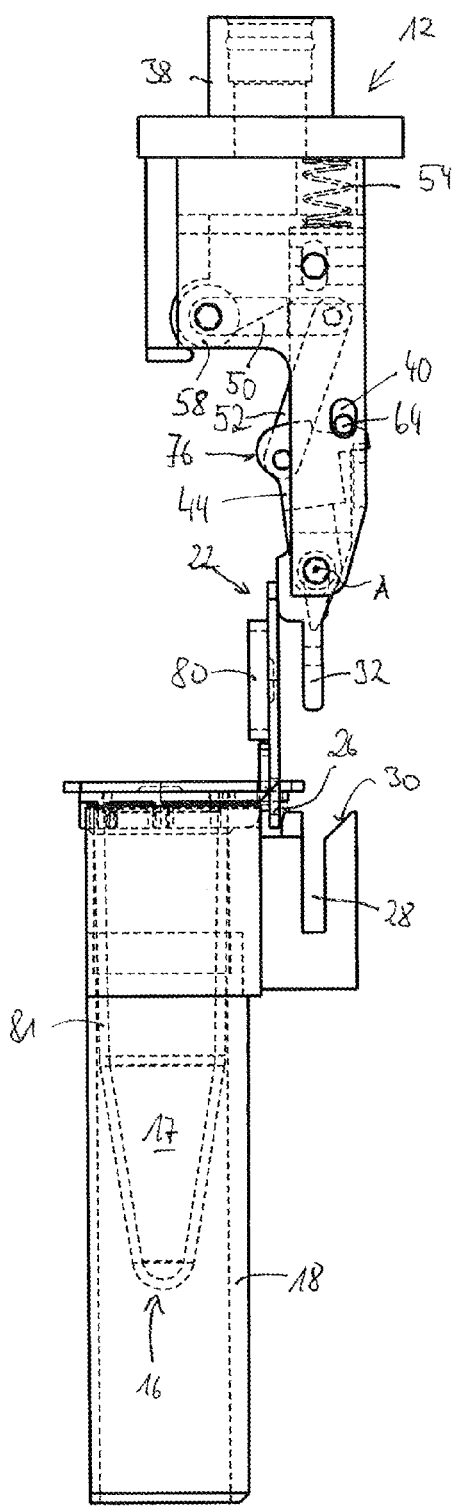
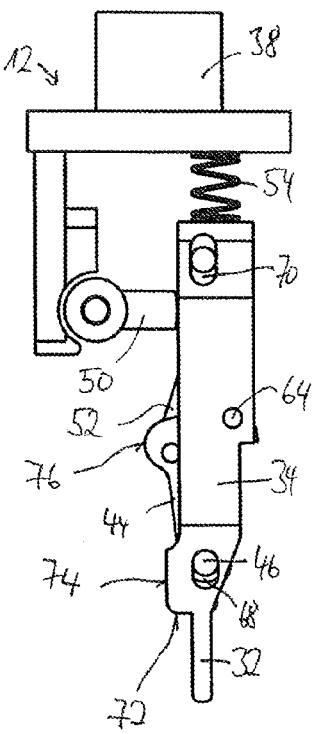
Fig. 7a:
Fig. 7b:

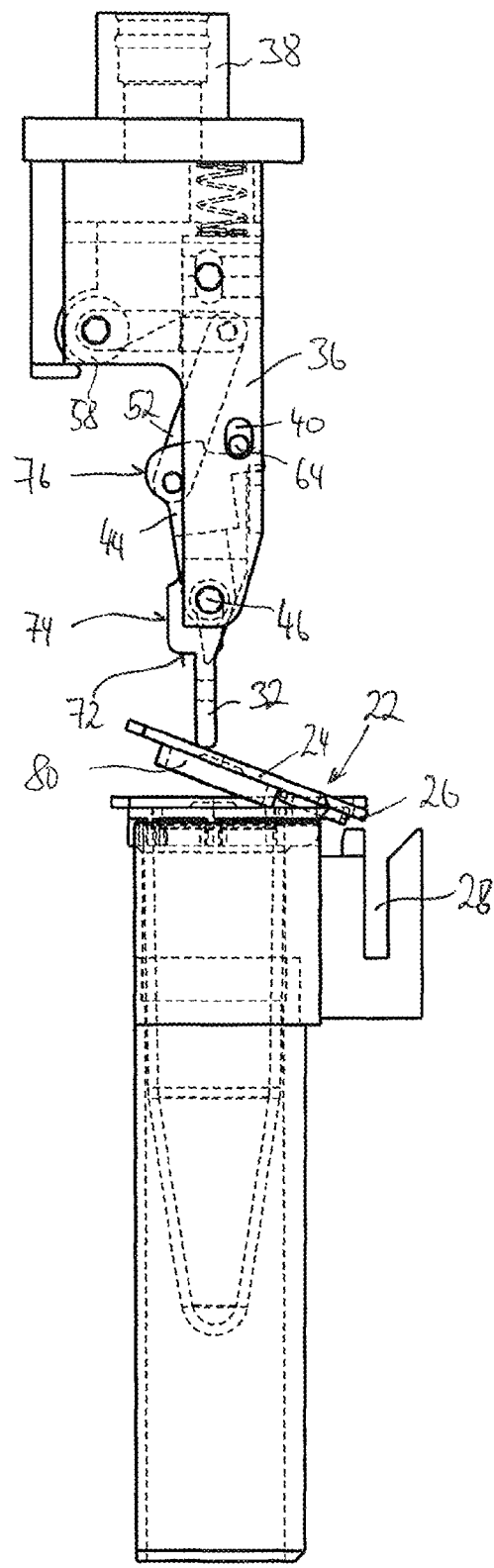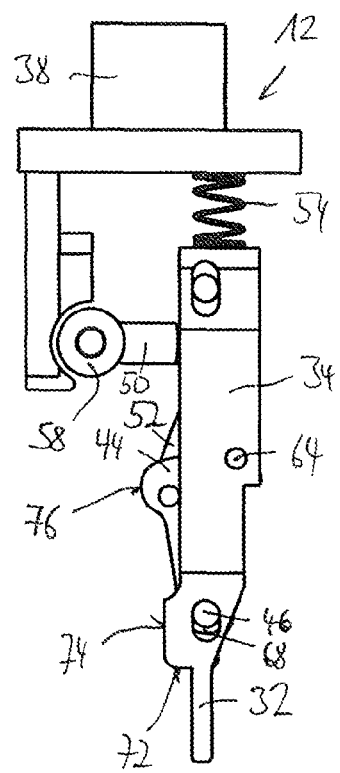

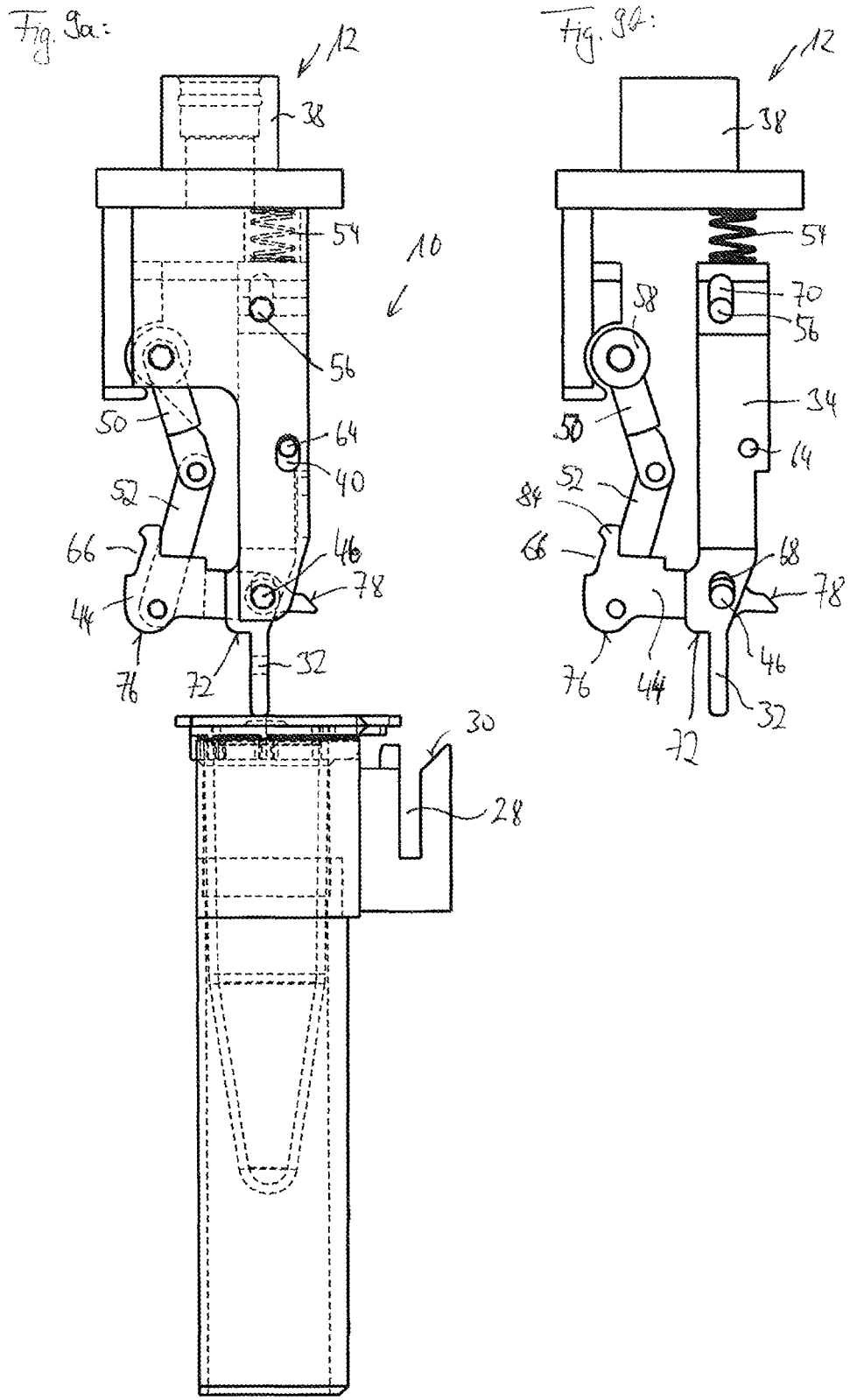

DEVICE FOR THE AUTOMATED OPENING OF FLIP TUBES

The present invention relates to a tool device for the automated opening of flip tubes and also relates to an assembly having a tool device of this type and having at least one container assembly which comprises at least one flip tube.

The term "flip tubes" denotes laboratory containers which are well known in the relevant technical field for storing liquids, where the interior of the basic body of a container is accessible through an opening in the container.

The container opening can be selectively closed by a container lid which can be swivelled about a lid swivel axis between an open position in which the interior of the container is accessible through the container opening, and a closed position in which the container opening is closed by the lid. In this respect, the container lid has on one side of the lid swivel axis a lid portion which selectively uncovers or closes the container opening and has on the respective other side of the lid swivel axis an actuating portion joined to the lid portion for joint movement therewith. Actuation of the actuating portion in an open direction causes the lid portion to swivel out of a position relatively close to the closed position, preferably out of the closed position itself, to a position relatively close to the open position, preferably into the open position itself. In laboratory technology, flip tubes of this type are considered useful particularly for the storage of liquids which are to be provided for dosage by pipette. The particular value of flip tubes is seen in the closing ability of the interior of the container, as a result of which a liquid received therein is protected to the greatest possible extent against external influences while the flip tube is closed.

However, the use of flip tubes is also associated with problems due to the closing ability thereof: the lid portion is often locked with the basic body of the container to secure the lid portion in the closed position, which is why an appreciable amount of force has to be applied to open a flip tube to release the locking of the lid portion in the closed position.

It is true that specifically the actuating portion described above was provided in an area away from the container opening, so that the flip tube could be opened without a laboratory technician having to grip the basic body of the container or the lid portion directly on the container opening by hand or using a tool. However, for the most part, flip tubes are opened suddenly, which can result in the liquid contained inside being undesirably shaken or even spilt.

This undesirable effect can be furthered by the equalisation of a vacuum of a gas column which is present in the container chamber above the liquid received therein and which can build up when the lock is undone, for example when the lid portion is moved in the sense of an increase in the volume of the container interior, without firstly becoming released from the basic body of the container. When the lid portion starts to be released from the basic body of the container, this vacuum is suddenly relieved, so that a gas which suddenly flows from outside into the container produces an additional undesirable agitation of the liquid provided in the flip tube.

It is therefore the object of the present invention to facilitate the handling of flip tubes, in particular to make it easy to open and close flip tubes in a reliable manner.

This object is achieved by a tool device for the automated opening of flip tubes, which device comprises an actuating plunger which is provided and configured to move the actuating portion of the flip tube at least in the open direction and thereby to exert an opening moment on the lid portion, and which also comprises a damping means which is configured to exert a damping moment on the lid portion at least during a period of the actuation of the actuating portion by the actuating plunger, said damping moment being less in amount and being in an opposite direction compared to the opening moment.

The actuating plunger can directly exert an opening moment, i.e. a torque in the open direction, on the actuating portion and thereby indirectly on the lid portion, so that the container lid and thereby in particular the lid portion can be removed from the container opening to enable access to the interior of the container through the container opening. Due to the actuating plunger, the flip tube can be opened without the basic body of the container or the container lid having to be grasped in the region of the container opening by an operator. Instead, the tool device can be guided by an automated operator device, for example a robot, which means that an operator no longer has to stay in the vicinity of the flip tube when the tube is opened. Consequently, the risk of contamination of the inside of the container is reduced. Although not preferred, the option of the tool device being used manually by an operator is nevertheless not ruled out in principle.

The damping means which is also provided can specifically reduce the opening moment, acting on the lid portion, by a damping moment, so that it is possible to avoid a sudden, abrupt uncovering of the container opening. The fact that the damping moment is less in amount and is oriented in the opposite direction compared to the opening moment ensures that the flip tube can be opened using the tool device described here.

In this respect, the damping means does not have to be active during the entire opening movement of the container lid. Likewise, the damping means does not have to act on the container lid from the start of the opening procedure onwards, although this is preferred.

Thus, for a rapid release of a possible locking, usually also present, of the lid portion in the closed position, it can be helpful if initially the opening moment acts fully in terms of amount on the container lid and if the damping means is only activated shortly before the ultimate release of the locking of the container lid in order to avoid as far as possible the undesirable abrupt opening of the flip tube described above.

In principle, the damping means can also engage directly on the actuating portion of the container lid, although this is not preferred. On the one hand, the actuating portion is covered by the actuating plunger when the flip tube is opened, so that only a small amount of available space remains for the engagement of the damping means. On the other hand, the lid portion is usually configured with a relatively large, possible contact surface and extends in particular to an area further removed radially from the lid swivel axis, so that a force engagement by the damping means directly on the lid portion can result in a very finely meterable damping moment when the available, relatively large work arm of the lid portion is utilised.

Moreover, the provision of the damping means can simplify the movement control of a preferably automated handling device which guides the tool device and which would otherwise have to take over the fine control of the opening moment via the movement control of the actuating plunger if the damping means is omitted, which would be associated with a considerable expense, particularly in view of the generally short work arm of the actuating portion. Furthermore, by providing a damping means separately from the actuating plunger, it is sufficient for the actuating plunger and/or the damping means to be merely configured for contact engagement with a respectively associated portion of the container lid, said contact engagement being particularly simple to produce.

A constructively simple and therefore preferred configuration of the damping means for exerting a damping moment on the container lid, advantageously on the lid portion thereof, can thus be formed in that the damping means has a contact arrangement which is configured for contact engagement with the lid portion and can be moved between an initial damping position which is associated with a position of the lid portion which is relatively close to the closed position and an end damping position which is associated with a position of the lid portion which is relatively close to the open position.

In principle, the damping effect of the contact arrangement can be produced by the gravitational effect of a component of the contact arrangement or of the entire contact arrangement.

However, the damping effect of the damping means, i.e. the damping moment exerted by the damping means on the container lid, in particular on the lid portion, can be adjusted to a substantially greater extent and/or substantially more accurately in that the contact arrangement cooperates with a force implement such that it can be moved from the initial damping position into the end damping position at least in portions against a force effect of the force implement. A preferred force implement which allows an effectively metered damping effect and only requires a small amount of installation space is a spring means, whether it is a helical spring, a flat spiral spring, an elastomer spring or a polymer spring.

To achieve the desired damping effect, it is indeed sufficient for the contact arrangement to be movable only in a predetermined movement portion of the contact arrangement and thereby of the container lid against the force effect of the force implement. However, the contact arrangement is preferably movable along its complete movement path from the initial damping position into the end damping position against the force effect of the force implement to avoid an undesirable jerky movement of the container lid in each lid position. Furthermore, cooperation between the force implement and the contact arrangement can produce a pretensioning of the contact arrangement towards the initial damping position.

In principle, it can be considered that the contact arrangement can be moved in a translatory manner along a straight movement path between the initial damping position and the end damping position, for example using a contact piston which is configured directly for contact engagement with the container lid, in particular with the lid portion thereof, and which can be pretensioned, for example by a compression spring, i.e. a helical spring, as the force implement, towards the contact engagement. As a result, a very slim contact arrangement can be obtained which, however, could require a considerable amount of installation space along the translatory movement path, for example to provide the spring excursion of the compression spring. Furthermore, a contact piston of this type should have a high-quality guidance in order to avoid, for example, malfunctions of the tool device caused by stick-slip effects of the contact piston.

However, since the container lid itself can be swivelled about a lid swivel axis, it is preferable for the contact arrangement to be able to swivel about a contact swivel axis between the initial damping position and the end damping position. In this case, even if the contact swivel axis and the lid swivel axis should diverge, by allowing a sliding contact engagement between the contact arrangement and the container lid, in particular the lid portion thereof, it is possible for the contact arrangement to follow the movement of the container lid from a position relatively close to the closed position to a position relatively close to the open position over a long movement portion and to provide its damping effect.

To facilitate the swivelling movement, following the container lid movement, of the contact arrangement, it is preferably provided that the contact swivel axis and the lid swivel axis are substantially parallel. As a result, the tool device can be realised requiring a very small construction space, without the risk of the contact arrangement, which is at least temporarily in contact engagement with the container lid, becoming jammed.

To provide the finest possible adjustability of the damping moment provided by the damping means and/or to arrange the force implement remotely in a space-saving manner, at a distance from the contact arrangement, it can be provided that the contact arrangement is connected to the force implement by a transmission. The term "transmission" in the context of this development of the present invention is understood as meaning any system of components which are arranged in a force transmission relationship to one another. A knee link rod assembly has proved to be a particularly advantageous transmission, in particular for the swivellable contact arrangement. Furthermore, one of the rods of the knee link rod assembly can then be coupled with a spring means, preferably with a compact torsion spring means, as the force implement, as a result of which the contact arrangement can finally be pretensioned towards contact engagement with the container lid.

When, for example, the actuating plunger has stopped acting on the actuating portion of the container lid of the flip tube, to prevent the damping means from exerting a damping moment, acting in the closed direction, on the container lid, without this damping moment being counteracted by a greater, in terms of amount, opening moment, i.e. to avoid an undesirable closing of the container lid after being opened, it is preferably provided that the contact arrangement can be fixed, preferably locked, particularly preferably locked in a releasable manner at least in its end damping position. In this respect, a positive fixing is preferable for safety reasons.

The advantageous fixability of the contact arrangement in the end damping position can be achieved in terms of construction in that the tool device has a fixing arrangement which can be adjusted between a fixed position in which the contact arrangement is fixed in its end damping position and a released position in which the contact arrangement is free for movement out of the end damping position towards the initial damping position.

The fixing arrangement is preferably pretensioned towards the fixed position to ensure that when the contact arrangement reaches its end damping position, a fixing is possible without further actuation. In the simplest case, the pretension can be provided by the weight of the fixing arrangement, but is advantageously provided by a force means, for example a spring pretensioning arrangement, pretensioned with a defined force in a desired pretensioning direction, which can then differ from the direction of the gravitational effect.

To be able to ensure that the actuating plunger performs a movement suitable for opening the flip tube, it can be provided that the tool device has a guide means which extends along a guide path and is provided and configured for guiding a movement at least of the actuating plunger along the guide path.

Since the actuating plunger usually only has to press on the actuating portion of the container lid, the guide path is preferably a straight guide axis which is particularly easy to realise.

In principle, it can be considered that the guide path guides any movement of the actuating plunger, for example also a movement of the actuating plunger into a parked position after the flip tube has been opened. However, the guide path preferably runs in the direction of an actuating movement of the actuating plunger, so that the guide means can guide an actuating movement of the actuating plunger.

For example, to avoid force peaks when the actuating plunger starts to work, it can be provided that the actuating plunger is accommodated on a tool frame such that it can move relative thereto. Thus, at the start of its actuating action, the actuating plunger can perform a movement in the tool frame which reduces force peaks. Furthermore, engagement formations can be provided on the tool frame, which are only to come into engagement after a specific time once the actuating plunger has started to work. This can also be achieved by the described movability of the actuating plunger relative to the tool frame, so that initially only the actuating plunger engages in an actuating manner on the actuating portion of the container lid and only when the relative movement path between actuating plunger and tool frame is at an end can further engagement formations provided on the tool frame engage with counter formations, for example on the flip tube or on a flip tube holder.

The movement of the movement plunger relative to the tool frame preferably runs along the guide path determined by the guide means.

To allow the actuating plunger to exert a force on the actuating portion even during its movement relative to the tool frame, it can be provided that the actuating plunger is coupled in terms of force transmission with a force device such that the actuating plunger can only move relative to the tool frame against a force of the force device at least in a relative movement direction.

If the force device is a spring device, a force exerted by the actuating plunger on the actuating portion can be introduced gently, i.e. cumulatively.

Furthermore, the previously mentioned force effect arrangements, such as force implement, force means and/or force device can also ensure an advantageous automatic resetting of the arrangement, cooperating therewith, into a starting position of the respective arrangement which is advantageous for the operation of the tool device.

The damping means is preferably provided on the tool frame, so that the actuating plunger is not only movable relative to the tool frame, but is also movable relative to the damping means. As a result, for example parts of the actuating plunger or components which are rigidly connected thereto can contribute to the formation of the above-mentioned fixing arrangement.

If the damping means is provided on the tool frame, the tool frame can act as a bearing for the contact arrangement, so that the contact arrangement can be movably connected to the tool frame. In this case, the reaction moment, acting on the contact arrangement, of the damping moment can be supported on the tool frame.

Likewise, the force implement can be coupled with the tool frame in a stable, force-supporting manner.

Furthermore, at least one transmission part of the transmission can also be accommodated on the tool frame, so that the forces conducted by the transmission can also be transferred on the tool frame in a stable manner. The transmission part accommodated on the tool frame is particularly preferably a rod of a knee link rod assembly.

If the contact arrangement is advantageously linked to the tool frame for the reasons mentioned above, the tool frame can be fixed in its end damping position using an advantageously low number of components, if at least one fixing part of the fixing arrangement is provided on the actuating plunger to be jointly moved with the actuating plunger. In this respect, for example to avoid force peaks, the fixing part can in turn have a particular movability relative to the actuating plunger, although a rigid connection between the fixing part and the actuating plunger is preferred, so that the fixing part participates in the movement of the actuating plunger. As already stated, if the actuating plunger is coupled with a force device, a pretension produced by the force device of the actuating plunger can be used for the releasable or unreleasable locking ability of the contact arrangement on the fixing part.

In order to be able to provide for the container lid a defined open position which can be achieved in a reproducible manner, it can also be provided that the tool device has a lid contact surface which is configured to rest against the container lid when the lid is in its open position. Furthermore, due to this lid contact surface, an undesirable automatic closing movement by the container lid out of the open position which has been reached can be avoided or at least made difficult, as long as a portion of the container lid rests against the lid contact surface.

Since in any case the actuating plunger is configured to actuate the actuating portion and is therefore located in terms of operation very close to the container lid, the lid contact surface is preferably configured on the actuating plunger, although this is not absolutely necessary.

For the intended movement of the actuating portion, the actuating plunger can have an actuating surface which is configured for contact engagement with the actuating portion.

Particularly simple in terms of construction, but very effective in contact effect, the actuating surface and the lid contact surface can enclose an angle, so that initially the actuating plunger can press with the actuating surface on the actuating portion and can displace the actuating portion in this manner, as a result of which the lid portion swivels about the lid swivel axis until it finally rests against the lid contact surface of the actuating plunger. To obtain the best possible accessibility to the container opening of the open flip tube, the actuating surface and the lid contact surface should preferably enclose a right angle.

In the previous description, the flip tubes have been mentioned merely to support the description of the tool device, because the tool device can be described most easily in respect of some aspects by the interaction with flip tubes which are known per se.

However, the present invention also relates to an assembly of a tool device, as described above and developed as appropriate, as well as of at least one container assembly which comprises at least one flip tube within the context of this application. Formations can be provided on the tool device, which interact with counter-formations on the container assembly, so that the effects described in the following can only be achieved by the assembly consisting of tool device and container assembly taken as a whole.

Thus, the previously mentioned guide means can have a guide shape which is configured for a guide engagement with a guide opposite shape provided on the container assembly. Consequently, during a movement of the actuating plunger relative to the container assembly, a desired relative positioning of actuating plunger and container assembly can be ensured, for example such that the actuating plunger engages, particularly with its actuating surface to exert the opening moment, with the actuating portion of the container lid and it remains engaged therewith.

In this respect, a shape consisting of the guide shape and the guide opposite shape can have a projection extending along the guide path and the respective other shape can have a recess corresponding to the projection.

Since the actuating portion of the container lid usually has an adequate length for actuation in its axial direction along the lid swivel axis, although the actuating portion is short in the radial direction away from the lid swivel axis and, moreover, changes its incline as the flip tube is progressively opened, it is preferable that the guide shape and the guide opposite shape ensure at least a defined radial distance of the actuating plunger from the lid swivel axis.

Although it can be considered that the guide shape and the guide opposite shape also ensure a fixing in position of the actuating plunger in the axial direction of the lid swivel axis during actuation of the actuating portion by the actuating plunger, this is less preferred, because a plurality of flip tubes is usually arranged spaced apart in the direction of the lid swivel axis in a container assembly, so that a particular movability of the actuating plunger in the direction of the lid swivel axis for the relatively rapid sequence of an actuation of axially adjacent flip tubes can even be desired.

The container assembly usually has one or more flip tubes, which are accommodated in a flip tube holder configured separately from the at least one flip tube. This makes it easy to change individual flip tubes. However, since the material of the flip tube holder is generally relatively rigid, it is then advantageous to configure the guide opposite shape in the flip tube holder, which improves the guide characteristics of the guide means.

To ensure that the container lid remains in its open position even after the tool device has been removed from a container lid which has just been swivelled into its open position, it can be provided that the assembly has a catch means which fixes the container lid in the open position. An advantageous fixing forms the above-mentioned locking, in which case it is then possible to manage with a particularly small number of moving parts if the locking is configured to be releasable, particularly due to material resiliences.

In this respect, it is preferred if the catch means is configured on the container assembly and particularly preferably on the flip tube holder which is configured separately from the at least one flip tube, because compared to the flip tube itself, the flip tube holder is usually the more rigid component, and thus is more suitable to provide the locking.

In terms of construction, the previously mentioned locking, configured to be releasable due to material resiliences, of the catch means can be realised in that the catch means comprises a catch projection which projects into the movement region of the actuating portion of the container lid such that, due to a resilience of the container lid, in particular of the actuating portion, and/or of the catch projection, it can be released from the container lid when it moves between the open position and the closed position.

Likewise, it can be desirable for the contact arrangement to be moved in a defined manner into its end damping position, particularly if it is configured to be able to swivel about a contact swivel axis. This can ensure that the contact arrangement also reaches its end damping position. In terms of construction, this can be easily achieved in that the contact arrangement has an end position shape which is configured for a guiding engagement with an end position opposite shape of the container assembly. For example, the end position shape and the end position opposite shape can be formed by corresponding bevels or curved surfaces, on which the end position shape and the end position opposite shape slide against one another with the formation of a positive guidance.

For the reasons mentioned above, the end position opposite shape of the container assembly is particularly preferably provided on a flip tube holder configured separately from the at least one flip tube.

Processing the opposite shapes advantageously provided on the assembly can be achieved in that the end position opposite shape and the guide opposite shape are arranged directly next to one another, preferably following one another along the guide path, so that the guide opposite shape and the end position opposite shape can advantageously be produced by machining using one and the same tool in a single clamp or, during primary shaping, an assembly can be provided with the smallest possible space requirement, while at the same time ensuring the above-mentioned guide objectives.

In the following, the present invention will be described in more detail with reference to the accompanying figures.

FIG. 1 is a perspective view of an assembly consisting of an embodiment according to the invention of a tool device and of a container assembly with at least one flip tube and a flip tube holder, FIG. 2a is a side view of the assembly from FIG. 1, viewed along the lid swivel axis, FIG. 2b shows the tool device of FIG. 2a, omitting parts of the tool frame, FIGS. 3a to 9b show the assembly and tool device of FIGS. 2a and 2b in further advanced processing situations of the opening and closing of a flip tube by the tool device.

In FIG. 1, an assembly, generally denoted by reference numeral 10, is shown in a perspective view and it comprises an embodiment according to the invention of a tool device 12 and a container assembly 14 with eight identical flip tubes 16, of which the two outermost flip tubes are held in legs 18 of a holder 20 configured separately from the flip tubes 16. The flip tubes 16 have a container lid 22 which can be swivelled about a lid swivel axis D out of the closed position shown in FIG. 1 in the direction of arrow O towards an open position. The flip tubes 16 of the holder 20 of FIG. 1 are arranged such that the lid swivel axes D thereof are arranged coaxially.

Each container lid 22 has a lid portion 24 which is located on one side of the lid swivel axis D, viewed from this axis, and has an actuating portion 26 which is preferably joined rigidly to the lid portion 24 so that it can be moved together therewith and is located on the side opposite the lid portion 24 with respect to the lid swivel axis D. The lid portion 24 and the actuating portion 26 preferably form a jointly outwardly directed planar lid surface 22a.

The holder 20 preferably has a guide groove 28 which forms a guide opposite shape within the context of the preceding introduction to the description. The guide groove 28 preferably runs continuously past all the flip tubes 16 parallel to the lid swivel axis D.

At the gap inlet end of the guide groove 28, a side 28a, defining the guide groove, has a bevel 30 which is inclined relative to the guide groove depth direction T orthogonal to the lid swivel axis D and which can advantageously serve on the one hand as an introduction bevel for a guide projection 32 of an actuating plunger 34 of the tool device 12, but which can also serve as the end position opposite shape in the context of the preceding introduction to the description, as will be described further below. The tool device 12 has, in addition to the aforementioned actuating plunger 34, a tool frame 36 which surrounds the actuating plunger 34 preferably in a forked manner on both side faces directed towards the lid swivel axis D and which can be coupled with a handling device, such as a robot, by a coupling geometry 38. In the preferred embodiment shown in FIG. 1, the actuating plunger 34 can be moved along the double arrow B relative to the tool frame 36, the double arrow B comprising the guide groove depth direction T in the arrangement shown in FIG. 1.

A slot 40, described in more detail further below, in the tool frame 36 indicates the relative movement stroke of the actuating plunger 34 relative to the tool frame 36.

As can also be seen in FIG. 1, the tool frame 36 can be constructed from a plurality of components.

The tool device 12 also comprises a damping means 42 with a contact arrangement 44 which can swivel about the contact swivel axis A.

The contact arrangement 44 is preferably extended from the tool frame 36 such that it can swivel thereon by a swivel pin 46, the centre axis of which forms the contact swivel axis A.

Furthermore, the contact arrangement 44 can be connected to the tool frame 36 by a transmission 48 which is preferably configured as a knee link rod assembly.

In this respect, a first rod 50 is advantageously coupled with the tool frame such that it can swivel about a first rod axis L1, and a second rod 52 is advantageously coupled with the first rod such that it can swivel about a second rod axis L2 and is coupled with the contact arrangement such that it can swivel about a third rod axis L3. The rod axes L1, L2 and L3 are parallel to one another and are preferably also parallel to the contact swivel axis A.

The first rod 50 is preferably pretensioned in the position shown in FIG. 1 by a pretensioning means, not shown in FIG. 1, so that the contact arrangement 44 is preferably also pretensioned in the initial damping position shown in FIG. 1 by this pretension.

FIG. 2*a* is an enlarged side view of the assembly 10 from FIG. 1. FIG. 2*b* shows the tool device 12 of FIG. 2*a* without parts of the tool frame 36.

As already stated, in the arrangement of FIGS. 1 and 2*a*, a flip tube 16 which is to be opened is closed by a container lid 22 which is in its closed position, and thus the container interior 17 of the flip tube 16 is inaccessible.

The damping means 42 of the tool device 12, more precisely the contact arrangement 44, is in its initial damping position which is a starting position for an opening procedure of the flip tube 16 by the tool device 12.

The actuating plunger 34 is pretensioned in the position shown in FIGS. 2*a* and 2*b* by an actuating plunger pretensioning spring 54, which is a compression spring, supported at one end on the actuating plunger 34 and at the other on the tool frame 36.

A supporting pin 56, which extends parallel to the swivel pin 46 and on which a side 58*a* of a contact arrangement pretensioning spring 58 can be supported, can be provided on the tool frame 36. A further side 58*b* of the contact arrangement pretensioning spring 58 can be supported on the link pin 60 defining the rod axis L2, as a result of which the contact arrangement 44 can be indirectly pretensioned in the initial damping position shown in FIGS. 1, 2*a* and 2*b* by the contact arrangement pretensioning spring 58 engaging on the transmission 48.

A fixing rod 64, which spans the receiving space 62 (see FIG. 1) in the actuating plunger 34 to receive the contact arrangement 44 and which can preferably extend into the slot 40 in the tool frame 36 to restrict the relative stroke between actuating plunger 34 and tool frame 36, can be provided on the actuating plunger 34.

As will be described further below, the contact arrangement 44 can have a catch recess 66 which is located in the engagement region of the fixing rod 46 on the actuating plunger 34 in the end damping position of the contact arrangement 44.

Since the contact arrangement 44 is preferably coupled with the tool frame 36 such that it can swivel thereon via the swivel pin 46, while the fixing rod 64 can be displaced with the actuating plunger 34 relative to the tool frame 36 along the double arrow B, the distance between fixing rod 64 and swivel pin 46 can thus be varied, in particular it can be increased starting from the distance shown in FIGS. 2*a* and 2*b*.

Therefore, the actuating plunger pretensioning spring 54 can also act as a pretensioning spring for the fixing rod 64 which preferably releasably pretensions the fixing rod 64 in the fixed position shown in FIG. 2*a*.

Just as the slot 40 in the tool frame 36 serves the movability of the actuating plunger 34 relative to the tool frame 36, the slots 68 and 70 (see FIG. 2*b*), which are in the actuating plunger 34 and surround the swivel pin 46 and the supporting pin 56, serve the movability of the actuating plunger 34 along the double arrow B.

An actuating contact surface 72 is preferably configured on the actuating plunger 34 for the defined actuation of the actuating portion 46. When the container lid 22 has arrived in its open position, it preferably rests against the lid contact surface 74 which can also be configured on the actuating plunger 34. It is particularly preferred for the actuating surface 72 and for the lid contact surface 74 to merge into one another and to enclose a right angle, as can be seen in FIGS. 2*a* and 2*b*.

Preferably configured on the contact arrangement 44 is a contact nose 76 which is configured for sliding contact on the container lid 22, preferably on the lid portion 24.

In the embodiment described here, the contact arrangement 44 has at its end opposite the contact nose 76 an end position shape 78 which can be formed as a simple bevel. As will be shown further below, the end position shape 78 can cooperate with the bevel 30, acting as the end position opposite shape, on the flip tube holder 20 during operation of the tool device 12 or of the assembly 10, for example by a sliding contact engagement, to ensure that the contact arrangement 44 arrives reliably in its end damping position at a desired time.

FIGS. 3*a* and 3*b* show the assembly 10 of FIGS. 2*a* and 2*b* in a more advanced position during the automated opening of the flip tube 16.

The guide projection 32 is partly introduced into the guide groove 28, so that the actuating surface 72 on the actuating plunger 34 has come into contact with the actuating portion 26 of the actuating lid 22.

In this respect, the actuating plunger 34 is moved in the direction of arrow B1 against the force of the actuating plunger pretensioning spring 54 relative to the tool frame 36, until the fixing rod 64 comes into contact with the upper (FIG. 3*a*) longitudinal end of the slot 40.

At the same time, the contact nose 76 of the contact arrangement 44 has come into contact engagement with the lid portion 24 of the container lid 22 and has been moved slightly out of the initial damping position of FIGS. 2*a* and 2b, when FIG. 3a is viewed clockwise, against the pretensioning force of the contact arrangement pretensioning spring 58 in the direction of the closed position.

The pretensioning force of the contact arrangement pretensioning spring 58 ensures a reliable contact of the contact arrangement 44 on the contact portion, associated therewith, of the container lid 22.

FIGS. 4a and 4b show the automated opening procedure of the flip tube 16 at a further advanced stage.

The guide projection 32 is immersed even further into the guide groove 28, as a result of which the actuating surface 72 exerts a force on the actuating portion 26 and thus an opening moment on the container lid 22. A locking, which is produced in the closed position of the container lid by the catch collar 80 on the inside of the lid portion 24 of the container lid 22 with the container basic body 81 of the flip tube 16, is released due to the exerted opening moment.

As a result of opening the container lid 22 by swivelling said lid about the lid swivel axis D, the contact arrangement 44 has been swivelled away from the original initial damping position towards the end damping position even further against the pretensioning force 58 of the contact arrangement, when FIGS. 4a and 4b are viewed in a clockwise direction.

Due to the spring characteristic of the contact arrangement pretensioning spring 58 and also due to the geometric conditions of the transmission 48 configured as a knee link rod assembly, the force, exerted by the contact arrangement 44 on the lid portion 24 in the closed direction, changes with the angular position of the contact arrangement 44 relative to the tool frame 36, as a result of which the damping moment which is exerted by the contact arrangement 44 on the lid portion 26 and acts in the closed direction also changes with the angular position of the contact arrangement 44 relative to the tool frame 36.

It can also be seen in FIG. 4a how the elastically deformable actuating portion 26 of the container lid 22 comes into contact at its free longitudinal end with a catch projection 82 on the flip tube holder 20. Due to the material resiliences which are present in the actuating portion 26 and/or in the catch projection 82, the actuating portion 26 can be swivelled past the catch projection 82 towards the open position of the container lid 22.

FIGS. 5a and 5b show the time at which the actuating portion 26 becomes free from the catch projection 82. The force required for this is applied by the actuating plunger 34, more precisely by the actuating surface 72 which can also have a curved surface portion. The contact arrangement 44 is still positioned on the lid portion 24 of the container lid 22 and exerts a damping moment, acting in the closed direction, on the container lid 22, which damping moment is, however, less in amount than the opening moment exerted on the actuating portion 26 by the actuating plunger 34.

FIG. 5a also shows that the end position shape 78 of the contact arrangement 44 comes into sliding contact with the end position opposite shape 30 on the flip tube holder 20 as the opening movement progresses slightly.

Due to the relative position of actuating plunger 34 and tool frame 36 and to the arrangement, caused thereby, of the fixing rod 64, an end nose 84 defining the catch recess 66 in the contact arrangement 44 in FIG. 5a can be swivelled under the fixing rod 64 in a clockwise direction so that the fixing rod 64 is finally in the region of the catch recess 66.

This position is shown in FIGS. 6a and 6b.

In FIG. 6a, the container lid 22 has arrived in its open position and a portion thereof rests against the lid contact surface 74 of the actuating plunger 34.

Furthermore, the actuating portion 26 has released the catch projection 82, so that the container lid 22 is also held in its open position by the catch positive locking of the actuating portion 26 with the catch projection 82, as long as a closing moment releasing this catch projection is not exerted on the container lid 22.

Since the container lid 22 has reached its open position, the actuating portion 26 cannot oppose the force opposing the spring force of the actuating plunger pretensioning spring 54, so that a movement of the actuating plunger 34 results relative to the tool frame 36 in the direction of arrow B2, more specifically driven by the force of the actuating plunger pretensioning spring 54.

As a result, the fixing rod 64 enters the catch recess 66 in the contact arrangement 44 which, in the meantime, is in the end damping position in which the catch recess 66 is arranged for positive engagement with the fixing rod 64. Thus, due to the pretensioning force of the actuating plunger pretensioning spring 54, the contact arrangement 44 is held positively in the end damping position by means of the fixing rod 64 which is pretensioned in its fixed position.

FIGS. 7a and 7b show how the tool device 12 can be raised with the actuating plunger 34 which is pretensioned in the direction of arrow B2 by the actuating plunger pretensioning spring 54 on the tool frame 36, and thus with the simultaneous pretensioning of the fixing rod 64 in the fixed position, starting from the open flip tube 16 in the direction of arrow B1. In this respect, the lid contact surface 74 can slide along the substantially planar lid outer surface 22a of the container lid 22, because the container lid 22 is locked in the attained open position by the actuating portion 26 on the catch projection 82.

FIG. 8a shows how the tool device 12, in particular the actuating plunger 34 and thereon particularly the free longitudinal end of the guide projection 32, can be used to close a flip tube 16.

In this respect, a closing moment acting in the closed direction can be exerted on the container lid 22, in particular on the lid portion 24 thereof, using the tool device 12, preferably via the free end of the guide projection 32.

The actuating portion 26 of the container lid 22, the catch projection 82 and the actuating plunger pretensioning spring 54 are preferably to be configured in respect of the resilience thereof such that the locking, formed by the actuating portion 26 and catch projection 82, of the container lid 22 in the open position can be released using the actuating plunger 34, without the actuating plunger pretensioning spring 54 being compressed by the reaction force acting on the actuating plunger 34 and thereby without the fixing rod 64 being undesirably moved out of its fixed position into its released position.

FIG. 9a shows the state of the tool device 12 after the production of a catching state of the container lid 22, in particular of the catch collar 80 on the lid portion 24 thereof, with the container basic body 81 of the flip tube 16. When the tool device 12 presses on the outer surface 22a of the container lid 22 in the direction of arrow B2 preferably at the free longitudinal end of the guide projection 32, so that a movement of the actuating plunger 34 relative to the tool frame 36 is produced in the direction of arrow B1, the fixing rod 64 is finally moved out of its fixed position pretensioned by the actuating plunger pretensioning spring 54 into its released position, so that there is no longer a positive engagement between the fixing rod 64 and the catch recess 66 on the contact arrangement 44. Subsequently, the contact arrangement 44 is moved into its initial damping position by the transmission 48 due to the pretensioning force of the contact arrangement pretensioning spring 58, so that the tool device 12 in FIGS. 9*a* and 9*b* is in substantially the same system state as in FIGS. 2*a* and 2*b* and is ready for a renewed opening procedure of a flip tube.

The invention claimed is:

1. Tool device for the automated opening of flip tubes each having a container interior accessible through a container opening in the flip tube, wherein the container opening is selectively closable by a container lid that is swivelable about a lid swivel axis between an open position in which the container interior is accessible through the container opening, and a closed position in which the container opening is completely closed by the container lid preventing access to the container interior, the container lid having on one side of the lid swivel axis a lid portion that selectively uncovers or closes the container opening, and has on the respective other side of the lid swivel axis an actuating portion joined to the lid portion for joint movement therewith, actuation of the actuating portion in an opening direction causing the lid portion to swivel out of the closed position to a position being closer to the open position wherein the device comprises an actuating plunger which is provided and configured to forcibly contact the actuating portion and thereby to exert an opening movement on the lid portion to release a locking of the lid with the container and to move the actuating portion at least in the opening direction, and wherein the device further comprises a damping device that exerts a damping moment on the container lid at least during a period of the actuation of the actuating portion by the actuating plunger, which damping moment is less in amount and is directed in an opposite direction compared to the opening direction, wherein the damping device is movable relative to the actuating plunger, and further wherein, during a beginning of the movement of the lid from the closed position in the opening direction to said position being closer to the open positon, the actuating plunger contacts the actuating portion without the dampening device exerting the damping moment so that the opening movement acts fully to release the locking of the lid, and subsequently, when the lid has reached a damping start position that is closer to the closed position than the open position, the actuating plunger still contacts the actuating portion to move the lid in the opening direction against the action of the damping device while the damping device exerts the damping moment.

2. Tool device according to claim 1, wherein the damping device has a contact arrangement which is configured for contact engagement with the lid portion and can be moved between an initial damping position which is associated with a position of the lid portion being closer to the closed position, and an end damping position which is associated with a position of the lid portion being closer to the open position.

3. Tool device according to claim 2, wherein the contact arrangement cooperates with a force implement such that it can be moved at least in portions out of the initial damping position into the end damping position against a force effect of the force implement.

4. Tool device according to claim 2, wherein the contact arrangement is swivelable about a contact swivel axis between the initial damping position and the end damping position.

5. Tool device according to claim 4, wherein the contact swivel axis and the lid swivel axis are parallel.

6. Tool device according to claim 3, wherein the contact arrangement is connected to the force implement by a transmission configured as a rod assembly having at least two rods pivotally connected to one another and to the contact arrangement.

7. Tool device according to claim 2, wherein the contact arrangement is releasably fixed at least in its end damping position.

8. Tool device according to claim 7, further comprising a fixing arrangement which can be moved between a fixed position in which the contact arrangement is fixed in its end damping position, and a released position in which the contact arrangement is free for a movement out of the end damping position towards the initial damping position.

9. Tool device according to claim 1, further comprising a guide means which runs along a guide path and is provided and configured to guide a movement at least of the actuating plunger along the guide path.

10. Tool device according to claim 9, wherein the guide path extends in the direction of an actuating movement of the actuating plunger.

11. Tool device according to claim 1, wherein the actuating plunger is accommodated on a tool frame such that it is movable relative thereto.

12. Tool device according to claim 11, wherein the actuating plunger is coupled in terms of force transmission with a force device such that the actuating plunger is only movable against a force of the force device relative to the tool frame at least in a relative movement direction.

13. Tool device according to claim 11, wherein the damping device is provided on the tool frame.

14. Tool device according to claim 6, wherein at least one transmission part of the transmission is accommodated on the tool frame.

15. Tool device according to claim 8, wherein at least one fixing part of the fixing arrangement is provided such that it moves together with the actuating plunger.

16. Tool device according to claim 1, wherein the tool device has a lid contact surface which is configured to contact the container lid when the container lid is in its open position.

17. Tool device according to claim 16, wherein the actuating plunger has an actuating surface which is configured for contact engagement with the actuating portion.

18. Tool device according to claim 1 wherein the damping device is spaced apart from the actuating portion.

19. Assembly comprising:
a tool device for the automated opening of flip tubes each having a container interior accessible through a container opening in the container, wherein the container opening is selectively closable by a container lid that is swivelable about a lid swivel axis between an open position in which the container interior is accessible through the container opening, and a closed position in which the container opening is completely closed by the container lid preventing access to the container interior, the container lid having on one side of the lid swivel axis a lid portion that selectively uncovers or closes the container opening, and has on the respective other side of the lid swivel axis an actuating portion joined to the lid portion for joint movement therewith, actuation of the actuating portion in an opening direction causing the lid portion to swivel out of a position being closer to the closed position to a position being closer to the open position wherein the device comprises an actuating plunger which is provided and configured to move the actuating portion at least in the opening direction and thereby to exert an opening moment on the lid portion, and wherein the device further comprises a damping device which is configured to exert a damping moment on the container lid simultaneously as the actuating plunger is forcibly contacting the actuating portion, which damping moment is less in amount and is directed in an opposite direction compared to the opening moment, wherein the damping device is movable relative to the actuating plunger; and at least one container assembly which comprises at least one flip tube.

20. Assembly according to claim 19, wherein the tool device further includes a guide means which runs along a guide path and is provided and configured to guide a movement at least of the actuating plunger along the guide path, and wherein the guide means has a guide shape which is configured for guide engagement with a guide opposite shape provided on the container assembly.

21. Assembly according to claim 19, wherein the container assembly has a flip tube and a flip-tube holder configured separately from this flip tube.

22. Assembly according to claim 19, wherein the assembly, has a catch means which releasably fixes the container lid in the open position.

23. Assembly according to claim 22, wherein the catch means comprises a catch projection which projects into the movement region of the actuating portion of the container lid such that it is capable of being overcome by the container lid when it moves between the open position and the closed position due to a resilience of the container lid.

24. Assembly according to claim 19, wherein the damping device has a contact arrangement which is configured for contact engagement with the lid portion and is movable between an initial damping position which is associated with a position of the lid portion being closer to the closed position, and an end damping position which is associated with a position of the lid portion being closer to the open position, and wherein the contact arrangement has an end position shape which is configured for guiding engagement with an end position opposite shape of the container assembly to support the attainment of the end damping position of the contact arrangement.

25. Assembly according to claim 24, wherein the tool device further includes a guide means which runs along a guide path and is provided and configured to guide a movement at least of the actuating plunger along the guide path, and wherein the guide means has a guide shape which is configured for guide engagement with a guide opposite shape provided on the container assembly, wherein the guide means has a guide shape which is configured for guide engagement with a guide opposite shape provided on the container assembly, the end position opposite shape and the guide opposite shape are arranged directly next to one another.

26. Assembly according to claim 19 wherein, during a beginning of movement of the lid from the closed position in the opening direction to said position being closer to the open positon, the actuating plunger contacts the actuating portion without the dampening device exerting the damping moment, and subsequently, when the lid has reached a damping start position that is closer to the closed position than the open position, the actuating plunger contacts the actuating portion to move the lid in the opening direction against the action of the damping device while the damping device exerts the damping moment.

* * * * *